(12) United States Patent
Sun et al.

(10) Patent No.: US 6,519,495 B1
(45) Date of Patent: Feb. 11, 2003

(54) RATE-ADAPTIVE THERAPY WITH SENSOR CROSS-CHECKING

(75) Inventors: Weimin Sun, Plymouth, MN (US); Bruce R. Jones, Hopkins, MN (US); Douglas J. Lang, Arden Hills, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 85 days.

(21) Appl. No.: 09/638,975

(22) Filed: Aug. 15, 2000

(51) Int. Cl.$^7$ ................................................ A61N 1/36
(52) U.S. Cl. ........................................... 607/18; 607/19
(58) Field of Search .............................. 607/17, 18, 19, 607/23, 24, 20

(56) References Cited

U.S. PATENT DOCUMENTS

| | | | | |
|---|---|---|---|---|
| 4,719,921 | A | 1/1988 | Chirife | 128/419 PG |
| 4,773,401 | A | 9/1988 | Citak et al. | 128/419 PG |
| 4,865,036 | A | 9/1989 | Chirife | 128/419 D |
| 4,873,980 | A | 10/1989 | Schaldach | 128/419 |
| 4,919,137 | A | 4/1990 | Schaldach | 128/419 PG |
| 4,926,863 | A | 5/1990 | Alt | 128/419 PG |
| 4,940,053 | A | 7/1990 | Mann et al. | 128/419 PG |
| 4,945,909 | A | 8/1990 | Fearnot et al. | 128/419 PG |
| 5,044,365 | A | * 9/1991 | Webb | 607/18 |
| 5,078,133 | A | 1/1992 | Heinz et al. | 128/419 PG |
| 5,154,171 | A | 10/1992 | Chirife | 128/419 PG |
| 5,156,147 | A | 10/1992 | Warren et al. | 128/419 PG |
| 5,168,869 | A | 12/1992 | Chirife | 128/419 PG |
| 5,170,785 | A | 12/1992 | Heinz et al. | 128/419 PG |
| 5,174,286 | A | 12/1992 | Chirife | 128/419 PG |
| 5,179,949 | A | 1/1993 | Chirife | 128/419 PG |
| 5,197,467 | A | 3/1993 | Steinhaus et al. | 128/419 PG |
| 5,226,413 | A | 7/1993 | Bennett et al. | 128/419 PG |
| 5,487,753 | A | 1/1996 | MacCarter et al. | 607/17 |
| 5,562,711 | A | 10/1996 | Yerich et al. | 607/17 |
| 5,645,575 | A | 7/1997 | Stangl et al. | 607/17 |
| 5,674,257 | A | * 10/1997 | Stroebel | 607/17 |
| 5,792,195 | A | 8/1998 | Carlson et al. | 607/17 |
| 5,931,858 | A | 8/1999 | Kadhiresan et al. | 607/20 |
| 6,055,454 | A | * 4/2000 | Heemels | 607/18 |
| 6,119,040 | A | 9/2000 | Chirife | 607/18 |

* cited by examiner

Primary Examiner—George R. Evanisko
Assistant Examiner—Roderick Bradford
(74) Attorney, Agent, or Firm—Schwegman, Lundberg, Woessner & Kluth, P.A.

(57) ABSTRACT

A method and system for automatically adjusting the operating parameters of a rate-adaptive cardiac pacemaker in which maximum exertion levels attained by the patient are measured at periodic intervals and stored in order to compute or update a maximum exercise capacity. The slope of the rate-response curve is then adjusted to map an exertion level corresponding to the updated maximum exercise capacity to a maximum allowable pacing rate. In accordance with the invention, a maximum exercise capacity is determined by cross-checking periodic maximum exertion level sensor values with a motion-level sensor value.

20 Claims, 2 Drawing Sheets

RATE-ADAPTIVE THERAPY WITH SENSOR CROSS-CHECKING

FIELD OF THE INVENTION

This invention pertains to systems and methods for cardiac rhythm management. In particular, the invention relates to a system and method for automatically adjusting the operating parameters of a rate-adaptive cardiac pacemaker.

BACKGROUND

A conventional cardiac pacemaker is an implantable battery-powered electronic device that responds to sensed cardiac events and elapsed time intervals by changing its functional states so as to properly interpret sensed data and deliver pacing pulses to the heart at appropriate times. The pacing pulses are delivered through a lead made up of electrodes on a catheter or wire that connects the pacemaker to the heart. Modern pacemakers are typically programmable so that they can operate in any mode which the physical configuration of the device will allow. Such modes define which heart chambers are paced, which chambers are sensed, and the response of the pacemaker to a sensed P wave or R wave. A three-letter code is used to designate a pacing mode where the first letter refers to the paced chamber(s), the second letter refers to the sensed chamber(s), and the third letter refers to the response. Additional sensing of physiological data allows some pacemakers to change the rate at which they pace the heart in accordance with some parameter correlated to metabolic demand. Such pacemakers, which are the primary subject of the present invention, are called rate-adaptive pacemakers.

The most common condition for which pacemakers are used is the treatment of bradycardia. Permanent pacing for bradycardia is indicated in patients with symptomatic bradycardia of any type as long as it is likely to be permanent or recurrent and is not associated with a transient condition from which the patient may recover. Atrio-ventricular conduction defects (i.e., AV block) that are fixed or intermittent and sick sinus syndrome represent the most common indications for permanent pacing. In chronotropically competent patients in need of ventricular pacing, atrial triggered modes such as DDD or VDD are desirable because they allow the pacing to track the physiologically normal atrial rhythm, which causes cardiac output to be responsive to the metabolic needs of the body. Atrial triggering modes are contraindicated, however, in patients prone to atrial fibrillation or flutter or in whom a reliable atrial sense cannot be obtained. In the former case, the ventricles will be paced at too high a rate. Failing to sense an atrial P wave, on the other hand, results in a loss of atrial tracking which can lead to negative hemodynamic effects because the pacemaker then reverts to its minimum ventricular pacing rate. In pacemaker patients who are chronotropically incompetent (e.g., sinus node dysfunction) or in whom atrial-triggered modes such as DDD and VDD are contraindicated, the heart rate is determined solely by the pacemaker in the absence of intrinsic cardiac activity. That heart rate is determined by the programmed escape intervals of the pacemaker and is referred to as the lower rate limit or LRL.

Pacing the heart at a fixed rate as determined by the LRL setting of the pacemaker, however, does not allow the heart rate to increase with increased metabolic demand. Cardiac output is determined by two factors, the stroke volume and heart rate, with the latter being the primary determinant. Although stroke volume can be increased during exercise, the resulting increase in cardiac output is usually not sufficient to meet the body's metabolic needs unless the heart rate is also increased. If the heart is paced at a constant rate, as for example by a VVI pacemaker, severe limitations are imposed upon the patient with respect to lifestyle and activities. It is to overcome these limitations and improve the quality of life of such patients that rate-adaptive pacemakers have been developed. Rate-adaptive pacemakers operate so as to vary the lowest rate at which the heart is allowed to beat in accordance with one or more physiological parameters related to metabolic demand.

The body's normal regulatory mechanisms act so as to increase cardiac output when the metabolic rate is increased due to an increased exertion level in order to transport more oxygen and remove more waste products. One way to control the rate of a pacemaker, therefore, is to measure the metabolic rate of the body and vary the pacing rate in accordance with the measurement. Metabolic rate can effectively be directly measured by, for example, sensing blood pH or blood oxygen saturation. Practical problems with implementing pacemakers controlled by such direct measurements, however, have led to the development of pacemakers that are rate-controlled in accordance with physiological variables that are indirectly reflective of the body's metabolic rate such as body temperature, ventilation rate, or minute ventilation. Minute ventilation varies almost linearly with aerobic oxygen consumption during exercise up to the anaerobic threshold and is the physiological variable that is most commonly used in rate-adaptive pacemakers to reflect the exertion level of the patient.

An even more indirect indication of metabolic rate is provided by the measurement of body activity or motion. Body activity is correlated with metabolic demand because such activity requires energy expenditure and hence oxygen consumption. An activity-sensing pacemaker uses a piezoelectric sensor or accelerometer inside the pacemaker case that responds to vibrations or accelerations by producing electrical signals proportional to the patient's level of physical activity.

In such rate-adaptive pacemakers that vary the pacing rate in accordance with a measured exertion level, the control system is generally implemented as an open-loop controller that maps a particular exertion level to one particular target heart rate. The mapping is accomplished by a rate-response curve which is typically a linear function (i.e., a straight line), but could also be some non-linear function as well such as a dual-slope curve or exponential curve. The rate-response curve is then defined with minimum and maximum target heart rates. A minimum target heart rate for a patient can be ascertained clinically as a heart rate adequate to sustain the patient at rest, while a maximum allowable target heart rate is defined with a formula that depends on the patient's age. The rate-response curve then maps a resting exertion level to the minimum heart rate and maps the maximum exertion level attainable by the patient, termed the maximum exercise capacity, to the maximum allowable heart rate. The responsiveness of the control system, defined as how the target heart rate changes with a given change in exertion level, depends upon the slope of the rate-response curve (or slopes in the case of a dual-slope curve) which is dictated by the defined maximum exercise capacity. If the maximum exercise capacity is incorrectly defined, the pacemaker's responsiveness will not be set to an appropriate level. An under-responsive pacemaker will unnecessarily limit exercise duration and intensity in the patient because the heart rate will not increase enough to match metabolic demand, while an over-responsive pacemaker can lead to palpitations and patient discomfort.

In order to define a patient's maximum exercise capacity, exercise testing can be performed to determine the maximum exertion level that the patient is capable of attaining. The pacemaker can then be programmed with that value with adjustments made during follow-up clinical visits. Exercise testing may not always be practical, however, and a patient's maximum exercise capacity can change over time due to, e.g., physical conditioning, illness, or recovery from illness, which increases the need for follow-up visits. Algorithms have therefore been developed that attempt to adjust the responsiveness of rate-adaptive pacemakers automatically in accordance with exertion level measurements made as the patient goes about ordinary activity. Determining a patient's maximum exercise capacity from periodic exertion level measurements, however, is problematical since it is not known how close to the true maximum a periodic maximum exertion level is.

SUMMARY OF THE INVENTION

The present invention relates to a method for automatically adjusting the responsiveness of a rate-adaptive pacemaker by estimating a maximum exercise capacity from periodic exertion level measurements. In accordance with the invention, exertion levels in the patient are measured by an exertion level sensor to determine a periodic maximum level. The periodic maximum exertion level is then cross-checked with a simultaneously taken activity level measurement to form an estimate of the patient's maximum exercise capacity.

In one embodiment, exertion levels are measured with a minute ventilation sensor, and activity levels are measured with an accelerometer, so that each measured minute ventilation may be associated with a simultaneously taken activity level measurement. In order to estimate the maximum minute ventilation attainable, which corresponds to the patient's maximum exercise capacity, a maximum minute ventilation together with its paired activity level is determined for each day (or other time period). The activity level measurement associated with the periodic maximum ventilation measurement is then cross-checked with the activity level measurement in order to estimate the maximum exercise capacity. The activity level measurement is mapped to a percentage of minute ventilation reserve, the minute ventilation reserve being the difference between a patient's resting and maximum attainable minute ventilation. The cross-checking may be performed by dividing the periodic maximum exertion level by the percentage of minute ventilation reserve represented by the activity level measurement. One or more such estimates are used to estimate the patient's maximum exercise capacity. In another embodiment, pairs of minute ventilation and activity level measurements are validated with previously stored pairs before being used to estimate maximum exercise capacity.

DESCRIPTION OF SPECIFIC EMBODIMENTS

Figure 1:
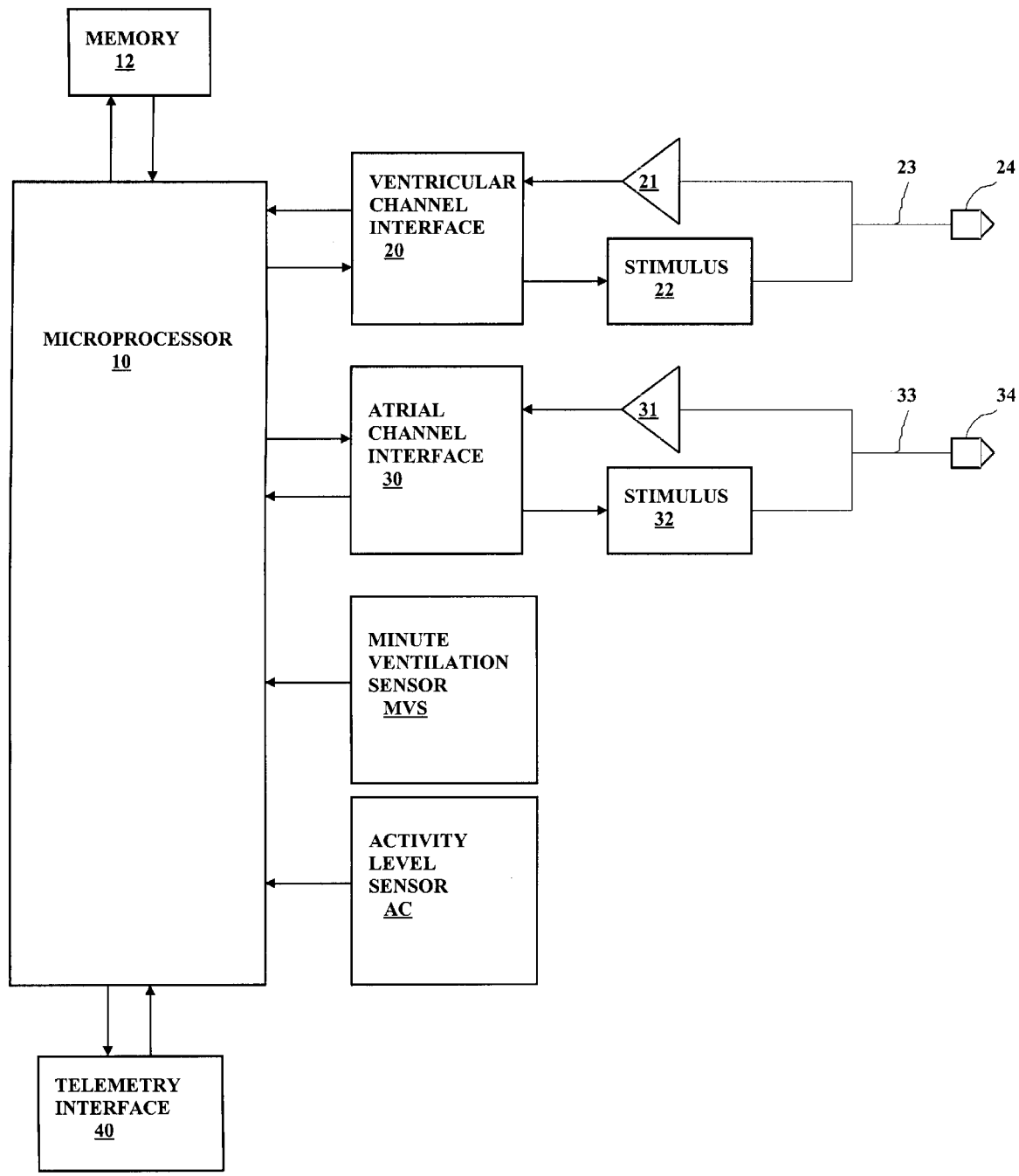
FIG. 1 is a diagram of a rate-adaptive pacemaker.

A particular implementation of a rate-adaptive pacemaker as shown in FIG. 1. As used herein, the term pacemaker should be taken to mean any cardiac rhythm management device with a pacing functionality including an implantable cardioverter/defibrillator that includes a pacemaker. A pacemaker controller senses cardiac events through a sensing channel and outputs pacing pulses to the heart via a pacing channel in accordance with a programmed pacing mode. A microprocessor serves as the controller in this embodiment and communicates with a memory 12 via a bidirectional data bus 13. The memory 12 typically comprises a ROM or RAM for program storage and a RAM for data storage. The pacemaker has atrial sensing and pacing channels comprising electrode 34, lead 33, sensing amplifier 31, pulse generator 32, and an atrial channel interface 30 which communicates bidirectionally with a port of microprocessor 10. The device also has ventricular sensing and pacing channels comprising electrodes 24, leads, sensing amplifier 21, pulse generator 22, and ventricular channel interface 20. For each channel, the same lead and electrode are used for both sensing and pacing. The channel interfaces 20 and 30 include analog-to-digital converters for digitizing sensing signal inputs from the sensing amplifiers and registers which can be written to by the microprocessor in order to output pacing pulses, change the pacing pulse amplitude, and adjust the gain and threshold values for the sensing amplifiers. A telemetry interface 40 is also provided for communicating with an external programmer. A minute ventilation sensor MVS and an accelerometer AC are employed to sense the minute ventilation and body activity, respectively. The pacemaker uses the sensed minute ventilation and/or the accelerometer signal to adjust the rate at which the pacemaker paces the heart in the absence of a faster intrinsic rhythm. The microprocessor 10 executes programmed instructions that implement various pacing and rate-adaptive algorithms, including the method for determining maximum exercise capacity as described below.

Figure 2:
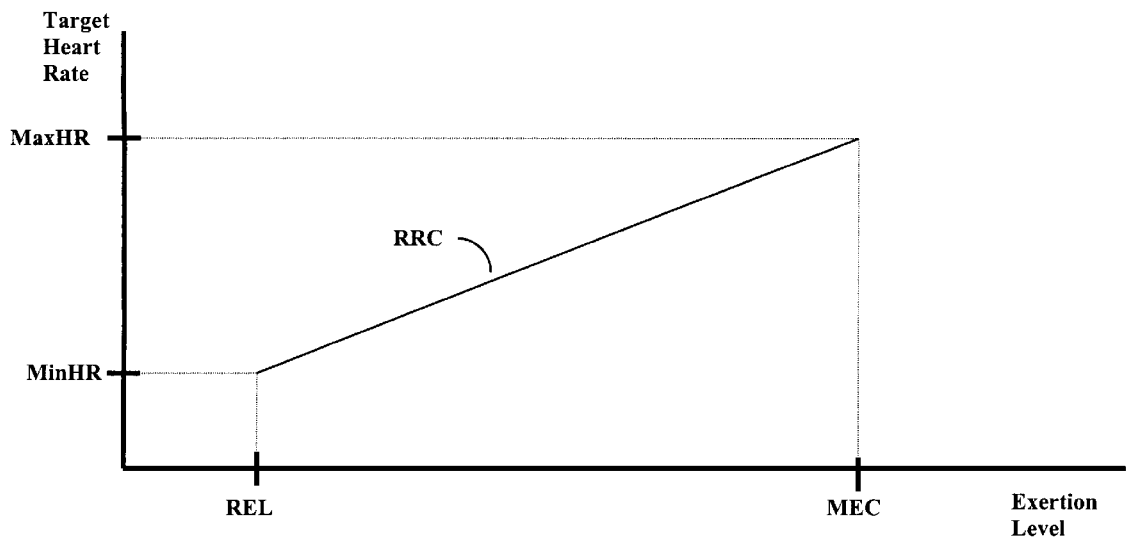
FIG. 2 depicts a rate-response curve.

The responsiveness of the pacemaker is controlled in accordance with a rate-response curve RRC as shown in FIG. 2. Other embodiments may use a dual-slope curve or a non-linear curve. A change in exertion level as determined from a minute ventilation measurement causes a proportional change in the target heart rate in accordance with the slope of the curve, termed the response factor RF. The target heart rate is then used as a lower rate limit (LRL) by the pacemaker to pace the heart in accordance with a programmed pacing mode. The LRL is the rate at which the heart is paced in the absence of faster intrinsic activity. As shown in the figure, the rate response curve maps a resting exertion level REL to a minimum target rate MinHR which corresponds to the minimum LRL that is to be used by the pacemaker. The maximum target rate MaxHR is the maximum rate at which the pacemaker is allowed to pace the heart and is mapped to by the rate response curve from the maximum exertion level the patient is expected to be able to reach, referred to as the maximum exercise capacity MEC. In the single-slope rate response curve shown in FIG. 2, the response factor RF may then be defined as:

$$RF = (MaxHR - MinHR)/(MEC - REL)$$

The minimum target rate and resting exertion level for a particular patient can be determined clinically after implantation. The maximum target rate can initially be determined from formulas derived from population data and dependent upon the patient's age or chosen by the physician. The responsiveness of the pacemaker is initially determined by setting the response factor RF to an initial value (e.g., 5) or by defining an initial maximum exercise capacity, which determines the endpoints and hence the slope of the rate response curve. An automatic parameter setting mode can then be employed so that the MEC and RF are changed from the initially set values in accordance with measurements of maximum exertion levels taken by the pacemaker. One way to do this is to monitor the patient's exertion levels, collect daily maximum exertion levels for a period of time (e.g., a week, a month, or six months), and select the highest exertion level among the daily maximums as an estimate of the patient's maximum exercise capacity. The rate response curve is then changed accordingly. Such a procedure allows the rate-adaptive pacemaker to be tuned to the individual patient as he goes about ordinary activities and also allows the pacemaker to adjust with changes in the patient's physical conditioning.

The procedure described above for estimating maximum exercise capacity uses a historical record of attained maximum exertion levels in order to lessen the likelihood of underestimation. That is, if the MEC were simply estimated as the maximum exertion level attained by the patient during a particular day, and the patient never actually exercised maximally during the day, the estimated MEC will be less than its true value. Setting the MEC lower than it should be causes the pacemaker to be over-responsive, the adverse clinical impact of which is potentially greater than if the pacemaker is made under-responsive. Estimating the MEC based upon historical measurements, however, necessarily delays the time before the responsiveness of the pacemaker can be adjusted.

In accordance with the present invention, an activity level measurement taken with a motion or pressure sensor such as an accelerometer is associated with a simultaneously taken exertion level measurement determined to be a maximum over a specified period. The periodic maximum exertion level measurement is then cross-checked with the associated activity level measurement to estimate the patient's maximum exercise capacity. A mapping based upon either population data or an assessment of the individual patient relates a particular activity level to a particular percentage of the patient's reserve exercise capacity. The reserve exercise capacity is defined as the difference between the maximum exercise capacity and the exertion level corresponding to rest. For example, a linear mapping may be used with a no-activity measurement value mapped to 0 percent of the reserve (i.e., the resting exertion level), a maximum activity measurement value mapped to 100 percent of the reserve (i.e., the maximum exercise capacity), and linearly interpolated values therebetween. The maximum exercise capacity is then estimated from the periodic maximum exertion level measurement based upon the percentage of the reserve exercise capacity that the associated activity level measurement corresponds to.

In one embodiment, for example, a minute ventilation sensor measures exertion levels of the patient and periodically (e.g., daily) records a maximum exertion level. Each recorded daily maximum exertion level is associated with an activity level measurement simultaneously taken with an accelerometer. The activity level measurement is mapped to a percentage of the patient's reserve exercise capacity, also referred to in this case as the minute ventilation reserve. The measured daily maximum minute ventilation is then cross-checked with the activity level measurement to estimate the patient's maximum exercise capacity. The cross-checking may be performed by dividing the measured maximum minute ventilation by the percentage of minute ventilation reserve represented by the activity level measurement. An updated response factor may then be computed from the estimate of maximum exercise capacity or from an average such estimates. If a minimum degree of responsiveness is desired, a minimum value for the response factor can be defined, or a minimum value can be defined for the percentage of reserve exercise capacity represented by an activity level measurement.

Figure 3:
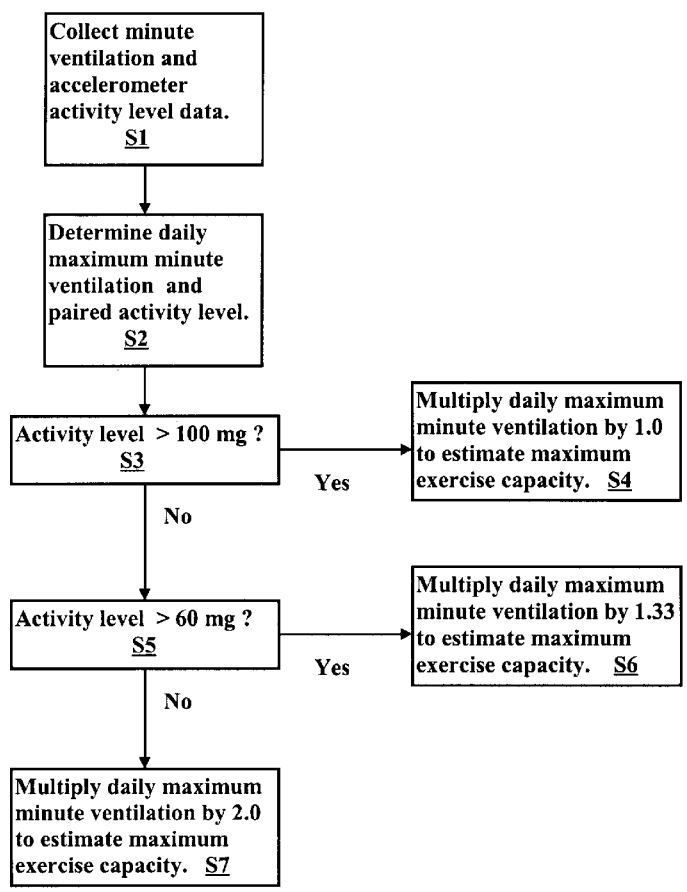
FIG. 3 is a flow chart illustrating a particular implementation of the present method.

Alternatively, the cross-checking of the periodic maximum exertion level may be performed with discrete percentages of reserve exercise capacity according to threshold values of measured activity levels. A range of measured activity level values then dictates the percentage that the periodic maximum exertion level is to be divided by in order to estimate the maximum exercise capacity. In an exemplary embodiment of the method illustrated in FIG. 3, two activity level thresholds are set at accelerometer measurements of 60 mg and 100 mg, representing minute ventilation reserves of 50 percent and 75 percent, respectively. At step S1, minute ventilation and accelerometer activity level data are collected during the day. Spurious peaks in the sensor signals can be removed with a moving average filter (e.g., 1 minute averages). At step S2, a daily maximum minute ventilation and an associated activity level are determined. Steps S3 and S5 test the activity level against the threshold activity level values. If the accelerometer measurement is greater than 100 mg, the maximum exercise capacity is estimated to be the same as the daily maximum minute ventilation at step S4. If the accelerometer measurement is greater than 60 mg but less than 100 mg, the maximum exercise capacity is estimated to be the daily maximum minute ventilation multiplied by 1.33 (i.e., divided by 75 percent) at step S6. If the accelerometer measurement is not greater than 60 mg, the maximum exercise capacity is estimated to be the daily maximum minute ventilation multiplied by 2.0 (i.e., divided by 50 percent) at step S7.

In another other embodiment, the maximum exercise capacity is estimated as the maximum among a plurality of historical daily maximums. The daily maximums are validated before being cross-checked with associated activity levels. A daily maximum and its associated activity level can also be validated by comparing them with past pairs. The daily maximum and associated activity level can then be used to compute the average or disregarded as spurious data. Still other embodiments may employ the estimated maximum exercise capacity to adjust the responsiveness of pacemakers with more complex rate-response curves (e.g., dual-slope or exponential).

Although the invention has been described in conjunction with the foregoing specific embodiment, many alternatives, variations, and modifications will be apparent to those of ordinary skill in the art. Such alternatives, variations, and modifications are intended to fall within the scope of the following appended claims.

What is claimed is:

1. A method for estimating a maximum exercise capacity in a patient, comprising:

measuring exertion levels attained by the patient and determining a periodic maximum exertion level;

measuring activity levels and associating the periodic maximum exertion level with a simultaneously taken activity level measurement; and, estimating the patient's maximum exercise capacity by cross-checking the periodic maximum exertion level with the simultaneously taken activity level measurement.

2. The method of claim 1 further comprising:

delivering paces to the heart in accordance with a rate-adaptive pacing mode;

adjusting a pacing rate by mapping a measured exertion level to a target pacing rate with a rate response curve defined with respect to a maximum exercise capacity; and, adjusting the slope of the rate response curve in order for the exertion level corresponding to the estimated maximum exercise capacity to be mapped to a specified maximum allowable pacing rate.

3. The method of claim 1 wherein exertion levels are measured with a minute ventilation sensor, and activity levels are measured with an accelerometer.

4. The method of claim 1 further comprising mapping an activity level to a percentage of reserve exercise capacity and performing the cross-checking by dividing the periodic maximum exertion level by the percentage of reserve exercise capacity mapped to by the activity level measurement.

5. The method of claim 4 wherein activity level measurements are mapped to a percentages of reserve exercise capacity by a linear relationship.

6. The method of claim 4 wherein activity level measurements are mapped to discrete percentages of reserve exercise capacity in accordance with threshold values of activity levels.

7. The method of claim 6 wherein exertion levels are measured with a minute ventilation sensor, activity levels are measured with an accelerometer, and accelerometer measurements are mapped to percentages of minute ventilation reserve in accordance with accelerometer threshold values representing minute ventilation reserve percentages.

8. The method of claim 7 wherein accelerometer measurements below a first threshold value of approximately 60 mg are mapped to 50% of minute ventilation reserve, accelerometer measurements above the first threshold and below a second threshold of approximately 100 mg are mapped to 75% of minute ventilation reserve, and accelerometer measurements above the second threshold are mapped to 100% of minute ventilation reserve.

9. The method of claim 1 wherein the periodic maximum exertion level is a daily maximum exertion level.

10. The method of claim 1 further comprising:
    determining a plurality of periodic maximum exertion levels;
    cross-checking the plurality of periodic maximum exertion levels; and,
    estimating the maximum exercise capacity as a maximum among the plurality of cross-checked periodic maximum exertion levels.

11. A rate-adaptive pacemaker, comprising:
    sensing channels for sensing atrial and ventricular depolarization signals, each channel including an electrode and a sense amplifier;
    a pulse generator for delivering pacing pulses to the atrium and/or ventricle;
    an exertion level sensor for measuring exertion levels;
    an activity level sensor for measuring activity levels; and,
    a processor for controlling the delivery of pacing pulses, wherein the processor is programmed to:
    adjust the rate at which paces are delivered by mapping a measured exertion level to a target pacing rate with a rate response curve defined with respect to a maximum exercise capacity, and
    estimate a patient's maximum exercise capacity by determining a periodic maximum exertion level and cross-checking the periodic maximum exertion level with a simultaneously taken activity level measurement.

12. The pacemaker of claim 11 wherein the processor is programmed to adjust the slope of the rate response curve in order for the exertion level corresponding to the estimated maximum exercise capacity to be mapped to a specified maximum allowable pacing rate by the rate response curve.

13. The pacemaker of claim 11 wherein the exertion level sensor is a minute ventilation sensor, and the activity level sensor is an accelerometer.

14. The pacemaker of claim 10 wherein the processor is programmed to perform the cross-checking by mapping the activity level measurement to a percentage of the patient's reserve exercise capacity and dividing the periodic maximum exertion level by the percentage of reserve exercise capacity mapped to by the activity level measurement.

15. The pacemaker of claim 14 wherein the processor is programmed to map activity level measurements to percentages of reserve exercise capacity by a linear relationship.

16. The pacemaker of claim 14 wherein the processor is programmed to map activity level measurements to discrete percentages of reserve exercise capacity in accordance with threshold values of activity levels.

17. The pacemaker of claim 16 wherein the exertion level sensor is a minute ventilation sensor, and the activity level sensor is an accelerometer, and the processor is programmed such that accelerometer measurements are mapped to percentages of minute ventilation reserve in accordance with accelerometer threshold values representing minute ventilation reserve percentages.

18. The pacemaker of claim 17 wherein accelerometer measurements below a first threshold value of approximately 60 mg are mapped to 50% of minute ventilation reserve, accelerometer measurements above the first threshold and below a second threshold of approximately 100 mg are mapped to 75% of minute ventilation reserve, and accelerometer measurements above the second threshold are mapped to 100% of minute ventilation reserve.

19. The pacemaker of claim 11 wherein the periodic maximum exertion level is a daily maximum exertion level.

20. The pacemaker of claim 11 wherein the processor is programmed to determine a plurality of periodic maximum exertion levels and estimate the maximum exercise capacity from a maximum among the plurality of cross-checked periodic maximum exertion levels.

* * * * *

UNITED STATES PATENT AND TRADEMARK OFFICE
CERTIFICATE OF CORRECTION

PATENT NO.    : 6,519,495 B1
DATED         : February 11, 2003
INVENTOR(S)   : Bruce R. Jones, Douglas J. Lang and Weimin Sun It is certified that error appears in the above-identified patent and that said Letters Patent is hereby corrected as shown below:

<u>Column 8,</u>
Line 18, delete "claim 10" and insert -- claim 11 -- therefor.

Signed and Sealed this

Second Day of December, 2003

JAMES E. ROGAN
*Director of the United States Patent and Trademark Office*